US009351683B2

(12) United States Patent
Yoshida

(10) Patent No.: US 9,351,683 B2
(45) Date of Patent: May 31, 2016

(54) WRINKLE DETECTION METHOD, WRINKLE DETECTION DEVICE AND RECORDING MEDIUM STORING WRINKLE DETECTION PROGRAM, AS WELL AS WRINKLE EVALUATION METHOD, WRINKLE EVALUATION DEVICE AND RECORDING MEDIUM STORING WRINKLE EVALUATION PROGRAM

(71) Applicant: FUJIFILM Corporation, Tokyo (JP)

(72) Inventor: Naoko Yoshida, Ashigara-kami-gun (JP)

(73) Assignee: FUJIFILM Corporation, Tokyo (JP)

(*) Notice: Subject to any disclaimer, the term of this patent is extended or adjusted under 35 U.S.C. 154(b) by 20 days.

(21) Appl. No.: 14/221,970

(22) Filed: Mar. 21, 2014

(65) Prior Publication Data
US 2014/0205159 A1  Jul. 24, 2014

Related U.S. Application Data

(63) Continuation of application No. PCT/JP2012/067572, filed on Jul. 10, 2012.

(30) Foreign Application Priority Data

Sep. 22, 2011 (JP) .................................. 2011-207296

(51) Int. Cl.
*G06T 7/00* (2006.01)
*A61B 5/00* (2006.01)
*A45D 44/00* (2006.01)

(52) U.S. Cl.
CPC ............... *A61B 5/442* (2013.01); *A61B 5/0077* (2013.01); *G06T 7/0085* (2013.01);
(Continued)

(58) Field of Classification Search
CPC .................. A61B 5/442; G06T 7/0085; G06T 2207/10004
See application file for complete search history.

(56) References Cited

U.S. PATENT DOCUMENTS 5,781,650 A * 7/1998 Lobo et al. .................... 382/118

FOREIGN PATENT DOCUMENTS

| EP | 1297782 A1 | 4/2003 |
| JP | 07-116146 A | 5/1995 |
| JP | 2010-119431 A | 6/2010 |

OTHER PUBLICATIONS

Chan, Chuan-Yi, Li, Shang-Cheng, Chung, Pau-Choo, Kuo, Jui-Yi, Yung-Chin, Tu. "Automatic Facial Skin Defect Detection System" 2010 International conference on Broadband, Wireless Computing, Communications and Applications.*

(Continued)

*Primary Examiner* — Kim Vu
*Assistant Examiner* — Molly Delaney
(74) *Attorney, Agent, or Firm* — Birch, Stewart, Kolasch & Birch, LLP

(57) ABSTRACT

A wrinkle detection method comprises the steps of obtaining face data of a subject; setting one or more analytical regions on the obtained face data; producing plural pieces of wrinkle component extracted data by extracting wrinkle components extending in one direction or in plural directions at different angles from each other in an angle range in which wrinkles tend to extend and which is set in advance for the set one or more analytical regions; producing plural pieces of wrinkle component emphasized data corresponding to the pieces of wrinkle component extracted data, respectively, by emphasizing the wrinkle components; producing composite data by combining the pieces of wrinkle component emphasized data; and detecting a wrinkle component having an intensity equal to or greater than a predetermined threshold value from the composite data as a wrinkle of the subject.

18 Claims, 2 Drawing Sheets

(52) U.S. Cl.
CPC ...... *A45D 2044/007* (2013.01); *A61B 2576/02* (2013.01); *G06T 2207/10004* (2013.01); *G06T 2207/20148* (2013.01); *G06T 2207/30201* (2013.01)

(56) References Cited

OTHER PUBLICATIONS

Ramanathan, Narayanan, Chellappa, Rama. "Face Verification Across Age Progression" IEEE Transaction on Image Processing Nov. 2006.*

International Preliminary Report on Patentability, and Translation of Written Opinion of the International Searching Authority, dated Apr. 3, 2014, for International Application No. PCT/JP2012/067572 (Forms PCT/IB/338, PCT/IB/373 and PCT/ISA/237).

Extended European Search Report dated Feb. 23, 2015, for European Application No. 12832858.0.

Marcos et al., "Nonverbal Communication with a Multimodal Agent via Facial Expression Recognition", IEEE International Conference on Robotics and Automation, May 9-13, 2011, pp. 1199-1204.

Martin-Vazquez et al., "A new user-friendly software platform for systematic classification of skin lesions to aid in their diagnosis and prognosis", Lasers Med Sci, vol. 21, 2006 (Published online Mar. 18, 2006), pp. 54-60.

"Guideline for Evaluation of Anti-wrinkle Products", Journal of Japanese Cosmetic Science Society, vol. 30, No. 4, pp. 316-332, 2006.

International Search Report for PCT/JP2012/067572 dated Oct. 9, 2012.

* cited by examiner

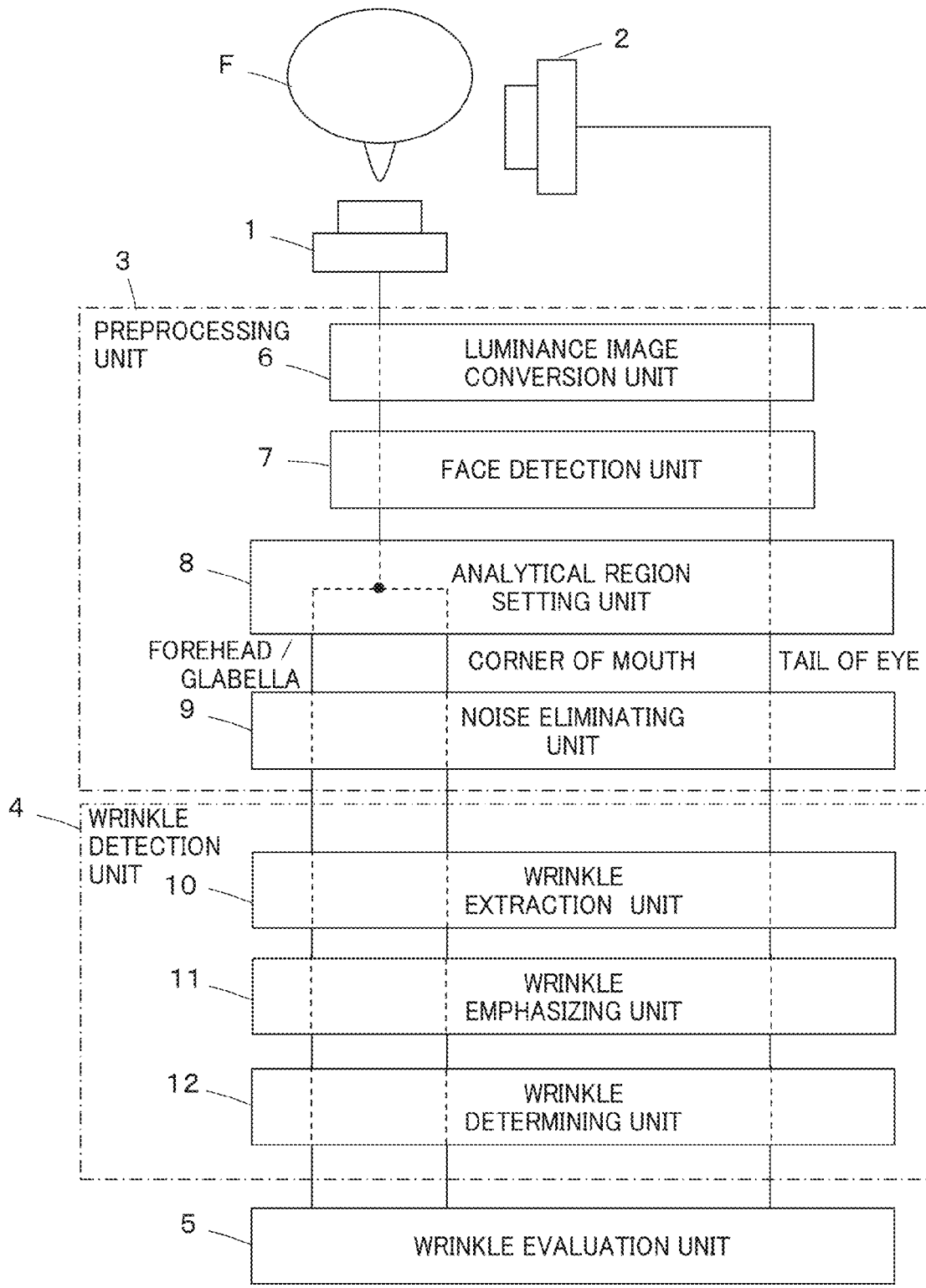

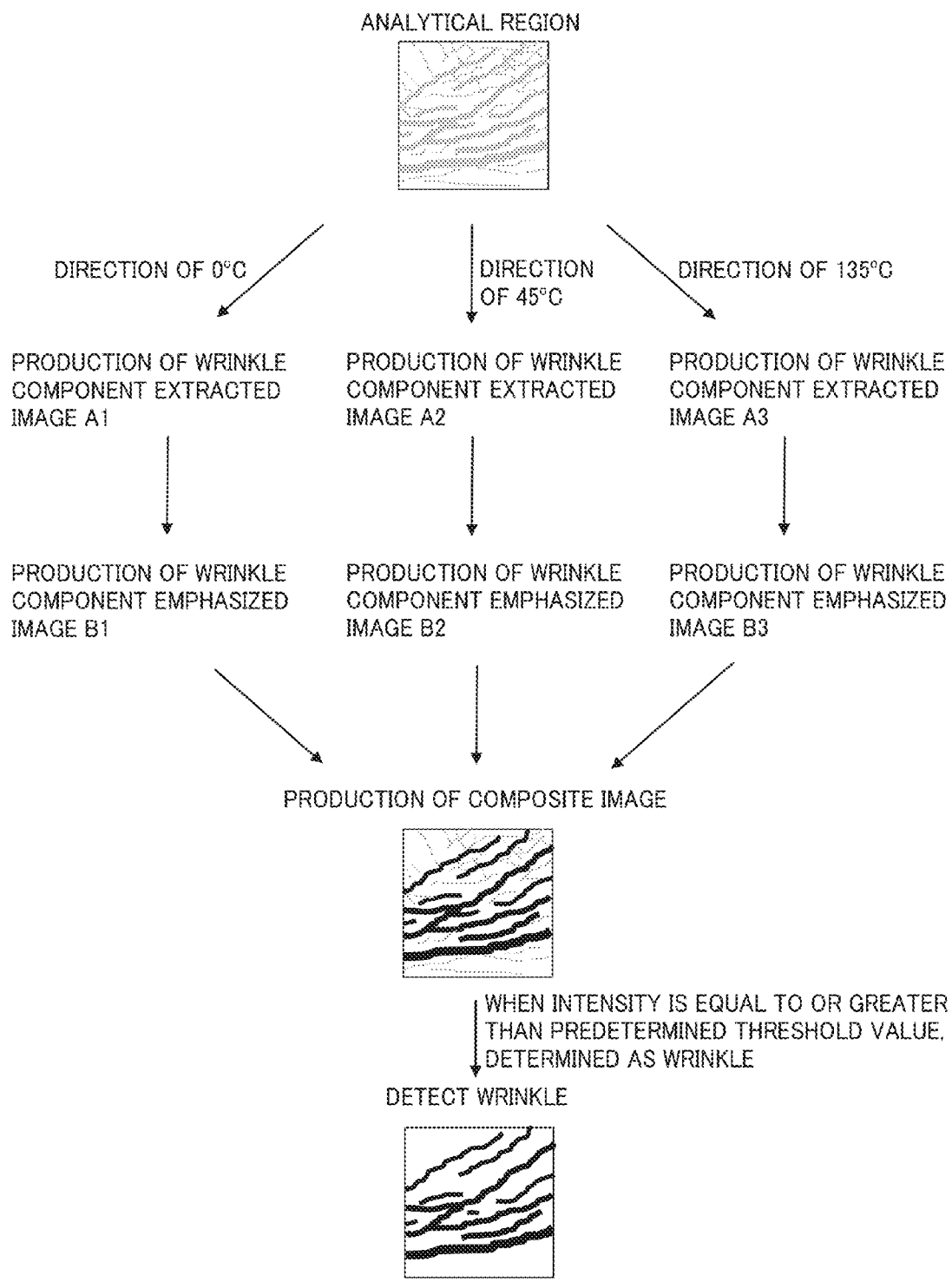

WRINKLE DETECTION METHOD, WRINKLE DETECTION DEVICE AND RECORDING MEDIUM STORING WRINKLE DETECTION PROGRAM, AS WELL AS WRINKLE EVALUATION METHOD, WRINKLE EVALUATION DEVICE AND RECORDING MEDIUM STORING WRINKLE EVALUATION PROGRAM

CROSS REFERENCE TO RELATED APPLICATIONS

This application is a continuation application of International Application PCT/JP2012/067572 filed on Jul. 10, 2012, which claims priority under 35 U.S.C. 119(a) to Application No. 2011-207296 filed in Japan on Sep. 22, 2011, all of which are hereby expressly incorporated by reference into the present application.

BACKGROUND OF THE INVENTION

The present invention relates to a method, apparatus and recording medium storing program for detecting wrinkles and a method, apparatus and recording medium storing program for evaluating wrinkles.

In human faces, wrinkles mainly appear on the forehead, on the glabella, in the corner of the mouth, at the tail of the eye, and the like. An area having wrinkles and the number of wrinkles differ from person to person. In the field of cosmetics, in order to provide cosmetics according to the state of wrinkles of each individual, the attempt to accurately detect wrinkles that appear at different portions in a face has been made.

For example, in a wrinkle detection method proposed by JP 07-116146 A, an image of a replica on which wrinkles of a subject are transferred is taken with a camera and based on data of the taken image, wrinkles are detected. By thus transferring wrinkles on a replica, image data of wrinkles can be stably obtained. However, direct application of a replica agent onto a face of the subject is required for the transfer of wrinkles, resulting in a great burden on the subject, so that it is desired to detect wrinkles without direct contact with the subject.

To cope with it, as an exemplary technique for detecting wrinkles without direct contact with a subject, JP 2010-119431 A proposes analyzing image data obtained by imaging a face of a subject based on the subject's wrinkle information extracted in advance. "Wrinkle Evaluation Guidelines" by Japanese Cosmetic Science Society proposes analyzing height data indicative of the asperities around wrinkles through non-contact three-dimensional measurement.

SUMMARY OF THE INVENTION

With the method stated in JP 2010-119431 A, when a lot of wrinkle information of many subjects can be extracted in advance, it is possible to accurately detect wrinkles of the subject. However, acquiring such wrinkle information in advance needs a substantial amount of work. In addition, an image obtained by imaging the face of the subject has many dark portions corresponding to other factors than wrinkles due to the asperity on the face, shades of the tail of the eye, color unevenness and flecks of the skin, and the like, and consequently portions other than wrinkles may be erroneously detected as wrinkles.

Also with the method stated in "Wrinkle Evaluation Guidelines" by Japanese Cosmetic Science Society, since there are many irregularities other than wrinkles, portions other than wrinkles may be erroneously detected as wrinkles.

An object of the present invention is to solve the foregoing drawbacks in the prior art and to provide a method and apparatus for detecting wrinkles which enable to reduce false detections when detecting wrinkles from an image obtained by imaging a face of a subject.

The present invention is also aiming to provide a method and apparatus for evaluating wrinkles having been detected by the wrinkle detecting method above.

A wrinkle detection method according to the present invention comprises the steps of: obtaining face data of a subject; setting one or more analytical regions on the obtained face data; producing plural pieces of wrinkle component extracted data by extracting wrinkle components extending in one direction or in plural directions at different angles from each other in an angle range in which wrinkles tend to extend and which is set in advance for the set one or more analytical regions; producing plural pieces of wrinkle component emphasized data corresponding to the pieces of wrinkle component extracted data, respectively, by emphasizing the wrinkle components;

producing composite data by combining the pieces of wrinkle component emphasized data; and detecting a wrinkle component having an intensity equal to or greater than a predetermined threshold value from the composite data as a wrinkle of the subject.

Preferably, the face data is obtained by converting image data acquired by imaging a face of the subject into a luminance image and detecting the face from the luminance image, and the wrinkle detection method comprises the steps of: setting the one or more analytical regions on the detected face; producing a plurality of wrinkle component extracted images as the plural pieces of wrinkle component extracted data by, from the set one or more analytical regions, extracting wrinkle components extending in one direction or in plural directions at different angles in an angle range in which wrinkles tend to extend and which is set in advance for the one or more analytical regions; producing a plurality of wrinkle component emphasized images as the plural pieces of wrinkle component emphasized data and corresponding to the wrinkle component extracted images, respectively, by emphasizing the wrinkle components; producing a composite image as the composite data by combining the wrinkle component emphasized images; and detecting a wrinkle component having an intensity equal to or greater than a predetermined threshold value from the composite image as the wrinkle of the subject.

The wrinkle component extracted images may be obtained by processing the one or more analytical regions with a plurality of wrinkle direction edge filters of different angles in the angle range; and the wrinkle component emphasized images may be obtained by reducing wrinkle orthogonal components orthogonal to the wrinkle components in the wrinkle component extracted images using a plurality of wrinkle orthogonal component extracted images obtained by processing the one or more analytical regions with a plurality of wrinkle orthogonal direction edge filters respectively orthogonal to the wrinkle direction edge filters.

Alternatively, the wrinkle component extracted images are obtained by processing the one or more analytical regions with a plurality of wrinkle direction edge filters of different angles in the angle range; and the wrinkle component emphasized images are obtained by calculating standard deviations among the wrinkle components in the corresponding wrinkle component extracted images and increasing a rate of emphasis at a portion with a standard deviation equal to or greater than a predetermined value.

The one or more analytical regions may be set at any of a forehead, a glabella, a corner of a mouth and a tail of an eye. Preferably, the face of the subject is captured from a front side and a left or right side; and the setting of the one or more analytical regions at the forehead, the glabella and the corner of the mouth is performed based on the luminance image captured from the front side, and the setting of the one or more analytical regions at the tail of the eye is performed based on the luminance image captured from the left or right side.

Preferably, the wrinkle direction edge filters are set in three directions in an angle range of 70 to 110 degrees when the one or more analytical regions are set at each of the forehead and the glabella, in eight directions in an angle ranges of 0 to 45 degrees and 115 to 165 degrees when the one or more analytical regions are set at the tail of the eye, and in six directions in an angle ranges of 45 to 60 degrees and 120 to 140 degrees when the one or more analytical regions are set at the corner of the mouth.

After the wrinkle component emphasized images in which the wrinkle components are emphasized are produced, noise may be eliminated from each of the wrinkle component emphasized images based on wrinkle shape information set in advance, and the wrinkle component emphasized images from which the noise has been eliminated are combined. Alternatively, after the wrinkle component emphasized images in which the wrinkle components are emphasized are produced, noise may be eliminated from each of the wrinkle component emphasized images by multiresolution method, and the wrinkle component emphasized images from which the noise has been eliminated are combined.

After the one or more analytical regions are set on the face, noise in the one or more analytical regions may be eliminated by Gaussian filtering or by performing quadric surface approximation on background luminance distribution, and the wrinkle component extracted images are produced from the one or more analytical regions, from which the noise has been eliminated, by extracting the wrinkle components.

A wrinkle evaluation method according to the present invention comprises the steps of: calculating amounts of characteristics of wrinkles such as the area, number, length, area ratio, width and depth thereof detected by the above-described wrinkle detection method; and evaluating degree of wrinkling by comparing the calculated amounts of characteristics such as the area, number, length, area ratio, width and depth, or a total value obtained by combining such indexes, with an average value of amounts of characteristics of wrinkles for a person at an age of the subject.

A wrinkle detection apparatus according to the present invention comprises a luminance image converter adapted to convert an image acquired by imaging a face of a subject into a luminance image; a face detector adapted to detect the face from the luminance image; an analytical region setting unit adapted to set one or more analytical regions on the detected face; a wrinkle extractor adapted to produce a plurality of wrinkle component extracted images by, from the set one or more analytical regions, extracting wrinkle components extending in plural directions at different angles in an angle range in which wrinkles tend to extend and which is set in advance for the one or more analytical regions; a wrinkle emphasizing unit adapted to produce a plurality of wrinkle component emphasized images corresponding to the wrinkle component extracted images, respectively, by emphasizing the wrinkle components and produce a composite image by combining the wrinkle component emphasized images; and a wrinkle determiner adapted to detect a wrinkle component having an intensity equal to or greater than a predetermined threshold value from the composite image as a wrinkle of the subject.

A wrinkle evaluation apparatus according to the present invention comprises the above-described wrinkle detection apparatus; and a wrinkle evaluator adapted to evaluate degree of wrinkling by calculating amounts of characteristics of a wrinkle detected by the wrinkle detection apparatus and comparing the calculated amounts of characteristics with an average value of amounts of characteristics of wrinkles for a person at an age of the subject.

A recording medium having stored therein a wrinkle detection program according to the present invention causing a computer to implement: a step of obtaining face data of a subject; a step of setting one or more analytical regions on the obtained face data; a step of producing plural pieces of wrinkle component extracted data by, from the set one or more analytical regions, extracting wrinkle components extending in one direction or in plural directions at different angles in an angle range in which wrinkles tend to extend and which is set in advance for the one or more analytical regions; a step of producing plural pieces of wrinkle component emphasized data corresponding to the pieces of wrinkle component extracted data, respectively, by emphasizing the wrinkle components; a step of producing composite data by combining the pieces of wrinkle component emphasized data; and a step of detecting a wrinkle component having an intensity equal to or greater than a predetermined threshold value from the composite data as a wrinkle of the subject.

A recording medium having stored therein a wrinkle evaluation program according to the present invention causing a computer to implement: a step of calculating amounts of characteristics of the wrinkle detected by the above-described wrinkle detection program; and a step of evaluating degree of wrinkling by comparing the calculated amounts of characteristics with an average value of amounts of characteristics of wrinkles for a person at an age of the subject.

According to the present invention, there are produced a plurality of wrinkle component extracted images that are obtained by, based on angles at which wrinkles tend to extend and which are set for respective portions of a face of a subject, extracting wrinkle components from a luminance image obtained by imaging the face, and the wrinkle components are emphasized in each of the produced wrinkle component extraction images, so that false detections can be reduced when detecting wrinkles from an image obtained by imaging the face of the subject.

BRIEF DESCRIPTION OF THE DRAWINGS

FIG. 1 is a block diagram showing the configuration of a wrinkle detection apparatus adapted to implement a wrinkle detection method according to an embodiment of the invention.

FIG. 2 is a diagram schematically showing a method for extracting wrinkles and a method for emphasizing wrinkles.

DETAILED DESCRIPTION OF THE INVENTION

An embodiment of the present invention will be described below based on the appended drawings.

FIG. 1 shows the configuration of a wrinkle detecting apparatus adapted to implement a wrinkle detecting method according to an embodiment of the invention. The wrinkle detecting apparatus has cameras 1 and 2, and a preprocessing unit 3, a wrinkle detection unit 4 and a wrinkle evaluation unit 5 are sequentially connected to the cameras 1 and 2.

The camera 1 is disposed to face a front side of a face F of a subject, and the camera 2 is disposed to face a lateral side of the face F of the subject.

The preprocessing unit 3 includes a luminance image conversion unit 6 connected to the cameras 1 and 2, and a face detection unit 7, an analytical region setting unit 8 and a noise eliminating unit 9 are sequentially connected to the luminance image conversion unit 6.

The luminance image conversion unit 6 converts images taken by the cameras 1 and 2 into luminance images. The face detection unit 7 detects a position of the face F of the subject as well as detecting feature portions such as the eyes, the eyebrows, the mouth and the nose from the luminance images produced by the luminance image conversion unit 6. The analytical region setting unit 8 sets analytical regions at predetermined portions at which wrinkles tend to appear, such as the forehead, the glabella, the corner of the mouth and the tail of the eye, for the face F of the subject detected by the face detection unit 7. The noise eliminating unit 9 eliminates the noise contained in the luminance images. For instance, the unevenness caused by light irradiation at the time of imaging the face F of the subject can be eliminated by smoothing the luminance image by Gaussian filtering or by performing quadric surface approximation on background luminance distribution.

The wrinkle detection unit 4 includes a wrinkle extraction unit 10 connected to the noise eliminating unit 9 of the preprocessing unit 3, and a wrinkle emphasizing unit 11 and a wrinkle determining unit 12 are sequentially connected to the wrinkle extraction unit 10.

The wrinkle extraction unit 10 has a built-in memory having stored therein angle ranges in which wrinkles tend to extend and which are set for respective portions of a face, and reads out from the memory angle ranges corresponding to the portions at which the analytical regions have been set by the analytical region setting unit 8. Subsequently, wrinkle components extending at different angles in the angle range as read out are separately extracted from the analytical region to produce a plurality of wrinkle component extracted images relevant to the respective different angles. The wrinkle component extracted images can be obtained by, for example, performing the processing on the analytical region with a plurality of wrinkle direction edge filters of different angles in the angle range read out from the memory to thereby increase the intensity of each wrinkle component in the analytical region depending on its angle direction.

The wrinkle emphasizing unit 11 produces a plurality of wrinkle component emphasized images by emphasizing wrinkle components in the wrinkle component extracted images produced by the wrinkle extraction unit 10. At that time, for instance, a plurality of wrinkle orthogonal component extracted images are produced by performing the processing on the analytical region with a plurality of wrinkle orthogonal direction edge filters respectively orthogonal to the wrinkle direction edge filters used in the extraction of the wrinkle components by the wrinkle extraction unit 10 so as to increase the intensity of each wrinkle orthogonal component orthogonal to a corresponding wrinkle component in the analytical region depending on its angle direction, and the wrinkle orthogonal component extracted images are used to reduce the wrinkle orthogonal components orthogonal to the wrinkle components in the wrinkle component extracted images, thereby obtaining the wrinkle component emphasized images. Further, the wrinkle emphasizing unit 11 combines the produced wrinkle component emphasized images to produce a composite image in which the wrinkle components are integrally emphasized in the analytical region.

The wrinkle determining unit 12 determines pixel-wise whether the intensity in the composite image is equal to or greater than a predetermined threshold value, and detects a wrinkle component having the intensity equal to or greater than the predetermined threshold value as a wrinkle of the subject.

The wrinkle evaluation unit 5 evaluates the degree of wrinkling by calculating the total area, number and length of the wrinkles detected by the wrinkle detection unit 4 and comparing the calculated area, number and length with the corresponding average for a person at an age of the subject.

It should be noted that the wrinkle direction edge filters used in the wrinkle extraction unit 10 and the wrinkle orthogonal direction edge filters used in the wrinkle emphasizing unit 11 are filters for extracting edge information in an image depending on the direction, and a Sobel filter, a first derivative filter, a Dog filter and the like may be utilized. In the case of using a Dog filter for example, two types of Gaussian images having different scales $\sigma$ are rendered to one-dimensional images, and the difference between the one-dimensional Gaussian images of two types is obtained to produce a one-dimensional Dog filter, i.e., a Dog filter exhibiting a certain directivity. Subsequently, the produced Dog filter is applied in a wrinkle direction or a wrinkle orthogonal direction, whereby edge information in the direction in question can be extracted from an image.

Next, a wrinkle detecting method implemented using the wrinkle detecting apparatus will be explained.

First, the front side of the face F of the subject is captured by the camera 1 while a lateral side thereof is captured by the camera 2. Image data of the front side and image data of the lateral side as obtained with the use of the cameras 1 and 2 are output to the luminance image conversion unit 6 of the preprocessing unit 3, and respectively converted to a front luminance image and a lateral luminance image by the luminance image conversion unit 6. The front luminance image and the lateral luminance image are output from the luminance image conversion unit 6 to the face detection unit 7. The face detection unit 7 detects the face F from the front luminance image and the lateral luminance image and also detects feature portions of the face F such as the eyes, the eyebrows, the mouth and the nose from the front luminance image as well as detecting one of the eyes as a feature portion of the face F from the lateral luminance image.

Then, based on the detection results of the face detection unit 7, the analytical region setting unit 8 sets analytical regions at predetermined portions at which wrinkles tend to appear in the face F. The analytical region setting unit 8 can set the analytical regions at the forehead, the glabella and the corner of the mouth for the front luminance image and at the tail of the eye for the lateral luminance image. The analytical regions thus set at the respective portions of the face F are output to the noise eliminating unit 9 to eliminate the noise and then output to the wrinkle extraction unit 10 of the wrinkle detection unit 4.

The wrinkle extraction unit 10 has stored in its built-in memory angle ranges in which wrinkles tend to extend and which are set for the respective predetermined portions of the face F, and reads out from the memory the angle ranges corresponding to the portions at which the analytical regions have been set by the analytical region setting unit 8. For example, when the analytical regions are set at the forehead and the glabella, the angle range of 70 to 110 degrees is read out; when the analytical region is set at the tail of the eye, the angle ranges of 0 to 45 degrees and 115 to 165 degrees are read out; and when the analytical region is set at the corner of the mouth, the angle ranges of 45 to 60 degrees and 120 to 140 degrees are read out, from the memory. Each analytical region is processed using a wrinkle direction edge filter of one arbitrary direction or wrinkle direction edge filters of plural directions at different angles in the relevant angle range as read out.

In the case where the analytical region is set at, for instance, the tail of the eye, wrinkle direction edge filters of three directions set at angles of 0 degrees, 45 degrees and 135 degrees may be used to process the analytical region, as shown in FIG. 2. As a result of this processing, the intensities of wrinkle components extending at angles of 0 degrees, 45 degrees and 135 degrees are increased, and a wrinkle component extracted image A1 obtained by extracting wrinkle components extending at an angle of 0 degrees, a wrinkle component extracted image A2 obtained by extracting wrinkle components extending at an angle of 45 degrees, and a wrinkle component extracted image A3 obtained by extracting wrinkle components extending at an angle of 135 degrees are separately produced. The wrinkle component extracted images A1, A2 and A3 obtained by extracting the wrinkle components extending at angles of the associated wrinkle direction edge filters are thus produced.

As described above, since a range to be subjected to the processing in an analytical region is narrowed down to a typical angle range in which wrinkles tend to extend and then the processing is performed using a relevant wrinkle direction edge filter, the amount of work required for the extraction of wrinkle components can be reduced. The produced wrinkle component extracted images A1, A2 and A3 together with the luminance images before the production of those images are output to the wrinkle emphasizing unit 11.

The wrinkle emphasizing unit 11 produces wrinkle component emphasized images B1, B2 and B3 in which the wrinkle components are relatively emphasized by reducing wrinkle orthogonal components orthogonal to the wrinkle components in the wrinkle component extracted images A1, A2 and A3 input.

To be more specific, using the luminance images before the production of the wrinkle component extracted images A1, A2 and A3, the analytical region is processed with wrinkle orthogonal direction edge filters of 90 degrees, 135 degrees and 45 degrees that are respectively orthogonal to the wrinkle direction edge filters of 0 degrees, 45 degrees and 135 degrees with which the wrinkle components have been extracted by the wrinkle extraction unit 10, so that wrinkle orthogonal component extracted images C1, C2 and C3 obtained by extracting the wrinkle orthogonal components orthogonal to the corresponding wrinkle components are produced. Subsequently, a combination of the wrinkle component extracted image A1 obtained by extracting the wrinkle components in the direction of 0 degrees and the wrinkle orthogonal component extracted image C1 obtained by extracting the wrinkle orthogonal components in the direction of 90 degrees is pixel-wise subjected to subtraction processing to thereby subtract the wrinkle orthogonal components in the direction of 90 degrees from the wrinkle components in the direction of 0 degrees. In the same manner, a combination of the wrinkle component extracted image A2 obtained by extracting the wrinkle components in the direction of 45 degrees and the wrinkle orthogonal component extracted image C2 obtained by extracting the wrinkle orthogonal components in the direction of 135 degrees as well as a combination of the wrinkle component extracted image A3 obtained by extracting the wrinkle components in the direction of 135 degrees and the wrinkle orthogonal component extracted image C3 obtained by extracting the wrinkle orthogonal components in the direction of 45 degrees are subjected to subtraction processing.

As a result, the wrinkle component emphasized images B1, B2 and B3 obtained by reducing the intensities of the wrinkle orthogonal components orthogonal to the wrinkle components in the wrinkle component extracted images A1, A2 and A3 can be produced, as shown in FIG. 2. Specifically, by reducing the intensities of the wrinkle orthogonal components that extend in the angle directions in which wrinkles hardly extend and are contained in the wrinkle component extracted images A1, A2 and A3, the wrinkle component emphasized images B1, B2 and B3 having the wrinkle components that extend in the angle directions in which wrinkles tend to extend and are relatively emphasized can be produced.

The wrinkle component emphasized images B1, B2 and B3 in which the wrinkle components are thus emphasized are combined to produce a composite image in which the wrinkle components are integrally emphasized in the analytical region. It should be noted that, before producing the composite image, the noise may be eliminated from the wrinkle component emphasized images B1, B2 and B3 based on wrinkle shape information such as the degree of circularity as set in advance, or may be eliminated from the wrinkle component emphasized images B1, B2 and B3 by multiresolution method, in order to combine the wrinkle component emphasized images B1, B2 and B3 from which the noise has been eliminated.

The composite image is output to the wrinkle determining unit 12 where it is determined pixel-wise whether the intensity in the composite image is equal to or greater than a predetermined threshold value, and a wrinkle component having the intensity equal to or greater than the predetermined threshold value is detected as a wrinkle of the subject.

Thus, the wrinkle orthogonal components extending in the angle directions in which wrinkles hardly extend, i.e., components other than wrinkles, can be removed from the composite image before the determination on wrinkles is carried out and therefore, false detections of wrinkles can be reduced.

The wrinkle components detected as wrinkles of the subject are output to the wrinkle evaluation unit 5 where the amount of characteristics such as the total area, number, total length, area ratio, width and depth of the wrinkles are calculated and the calculated results of the amount of characteristics are respectively compared to the corresponding average for a person at an age of the subject, thereby evaluating the degree of wrinkling.

Since the degree of wrinkling are thus calculated based on the wrinkle detection results with reduced false detections, the evaluation of wrinkles can be accurately carried out.

The wrinkle detection as described above can be performed by operating a computer composed of input unit, a CPU, a memory, a recording medium having stored therein a wrinkle detection program and the like. Specifically, the wrinkle detection program works to operate the computer so that the input unit acquires an image obtained by imaging a face of a subject and the CPU works to operate the preprocessing unit 3 and the wrinkle detection unit 4 to detect wrinkles based on the acquired image.

The wrinkle evaluation can also be performed by operating a computer having a recording medium having stored therein a wrinkle evaluation program. Specifically, the wrinkle evaluation program works to operate the computer so that a CPU works to operate the wrinkle evaluation unit 5 to evaluate wrinkles.

It should be noted that, in the foregoing embodiment, although the wrinkle emphasizing unit 11 produces the composite image after the wrinkle orthogonal components are removed from the wrinkle component extracted images produced by the wrinkle extraction unit 10, the invention is not limited thereto as long as the wrinkle orthogonal components can be reduced in the composite image, and the wrinkle orthogonal components may be removed after the composite image is produced.

It should also be noted that, although the wrinkle emphasizing unit 11 produces the wrinkle component emphasized images in which the wrinkle components are emphasized by removing the wrinkle orthogonal components from the wrinkle component extracted images produced by the wrinkle extraction unit 10, the invention is not limited thereto. For instance, when standard deviations among the wrinkle component extracted images are calculated, a standard deviation is to be higher at a wrinkle component. Hence, wrinkle component emphasized images can be obtained by calculating standard deviations among wrinkle components in the corresponding wrinkle component extracted images and by increasing a rate of emphasis at a portion where a standard deviation is equal to or greater than a predetermined value. The thus-produced wrinkle component emphasized images are combined to produce a composite image in which the wrinkle components are integrally emphasized in the analytical region.

It is preferred for the wrinkle extraction unit 10 to, in the case that the analytical regions are set at the forehead and the glabella by the analytical region setting unit 8, process the analytical regions with wrinkle direction edge filters set in three directions in the angle range of 70 to 110 degrees, in the case that the analytical region is set at the tail of the eye, process the analytical region with wrinkle direction edge filters set in eight directions in the angle ranges of 0 to 45 degrees and 115 to 165 degrees, and in the case that the analytical region is set at the corner of the mouth, process the analytical region with wrinkle direction edge filters set in six directions in the angle ranges of 45 to 60 degrees and 120 to 140 degrees. In addition, in order to prevent the processing of the analytical regions from varying, processing directions of the wrinkle direction edge filters are preferably set at regular intervals in the relevant angle ranges. The wrinkle orthogonal direction edge filters may be so set as to correspond to the wrinkle direction edge filters used in the processing of the analytical regions in a manner orthogonal thereto.

It should also be noted that, in the foregoing embodiment, although the cameras 1 and 2 are respectively disposed to face the front side and a lateral side of the face F of the subject, the invention is not limited thereto and three or more cameras may be disposed around the face F of the subject. For example, cameras may be disposed to face the front side and the both lateral sides of the face F. Alternatively, only one of the cameras 1 and 2 may be installed and the other camera may be moved around the face F of the subject to capture the face F.

It should also be noted that, in the foregoing embodiment, although wrinkles are detected based on the image data obtained using the cameras 1 and 2, the invention is not limited thereto as long as face data to be used for detecting wrinkles can be obtained. For example, face measurement data obtained by measuring the asperity of the face F of the subject through non-contact three-dimensional measurement may be used. Based on the face measurement data, analytical regions are set at predetermined portions at which wrinkles tend to appear in the face F, and after the noise is eliminated, wrinkles are detected in the same manner as above. Specifically, for each of the set analytical regions, plural pieces of wrinkle component extracted data are produced by, with the use of wrinkle direction edge filters, extracting wrinkle components extending in one direction or in plural directions at different angles in an angle range in which wrinkles tend to extend and which is set in advance for each of the predetermined portions in the face F. Then the plural pieces of wrinkle component extracted data are separately processed using wrinkle orthogonal direction edge filters to produce plural pieces of wrinkle component emphasized data in which the wrinkle components are emphasized, and the plural pieces of wrinkle component emphasized data as produced are combined to produce a composite data. Finally, the wrinkle components having the intensity equal to or greater than a predetermined threshold value in the composite data are detected as wrinkles of the subject.

What is claimed is:
1. A wrinkle detection method, comprising the steps of:
    storing in a memory in advance angle ranges in which wrinkles tend to extend and which are set for respective portions of a face;
    obtaining face data of a subject;
    setting one or more analytical regions on the obtained face data;
    reading out from the memory an angle range corresponding to each of the portions at which the one or more analytical regions have been set;
    processing each of the one or more analytical regions with a plurality of wrinkle direction edge filters of plural directions at different angles in the read out angle range to produce plural pieces of wrinkle component extracted data by extracting wrinkle components extending in one direction or in plural directions at different angles from each other in the read out angle ranges;
    producing plural pieces of wrinkle component emphasized data corresponding to the pieces of wrinkle component extracted data, respectively, by emphasizing the wrinkle components;
    producing composite data by combining the pieces of wrinkle component emphasized data; and
    detecting a wrinkle component having an intensity equal to or greater than a predetermined threshold value from the composite data as a wrinkle of the subject.
2. The wrinkle detection method according to claim 1, wherein the face data is obtained by converting image data acquired by imaging a face of the subject into a luminance image and detecting the face from the luminance image, and the wrinkle detection method comprises the steps of:
    setting the one or more analytical regions on the detected face;
    producing a plurality of wrinkle component extracted images as the plural pieces of wrinkle component extracted data by, from the set one or more analytical regions, extracting wrinkle components extending in one direction or in plural directions at different angles in an angle range in which wrinkles tend to extend and which is set in advance for the one or more analytical regions;
    producing a plurality of wrinkle component emphasized images as the plural pieces of wrinkle component emphasized data and corresponding to the wrinkle component extracted images, respectively, by emphasizing the wrinkle components;
    producing a composite image as the composite data by combining the wrinkle component emphasized images; and
    detecting a wrinkle component having an intensity equal to or greater than a predetermined threshold value from the composite image as the wrinkle of the subject.

3. The wrinkle detection method according to claim 2, wherein the wrinkle component emphasized images are obtained by reducing wrinkle orthogonal components orthogonal to the wrinkle components in the wrinkle component extracted images using a plurality of wrinkle orthogonal component extracted images obtained by processing the one or more analytical regions with a plurality of wrinkle orthogonal direction edge filters respectively orthogonal to the wrinkle direction edge filters.

4. The wrinkle detection method according to claim 2, wherein the wrinkle component emphasized images are obtained by calculating standard deviations among the wrinkle components in the corresponding wrinkle component extracted images and increasing a rate of emphasis at a portion with a standard deviation equal to or greater than a predetermined value.

5. The wrinkle detection method according to claim 3, wherein the one or more analytical regions are set at any of a forehead, a glabella, a corner of a mouth and a tail of an eye.

6. The wrinkle detection method according to claim 4, wherein the one or more analytical regions are set at any of a forehead, a glabella, a corner of a mouth and a tail of an eye.

7. The wrinkle detection method according to claim 5, wherein the face of the subject is captured from a front side and a left or right side; and
wherein the setting of the one or more analytical regions at the forehead, the glabella and the corner of the mouth is performed based on the luminance image captured from the front side, and the setting of the one or more analytical regions at the tail of the eye is performed based on the luminance image captured from the left or right side.

8. The wrinkle detection method according to claim 6, wherein the face of the subject is captured from a front side and a left or right side; and
wherein the setting of the one or more analytical regions at the forehead, the glabella and the corner of the mouth is performed based on the luminance image captured from the front side, and the setting of the one or more analytical regions at the tail of the eye is performed based on the luminance image captured from the left or right side.

9. The wrinkle detection method according to claim 5, wherein the wrinkle direction edge filters are set in three directions in an angle range of 70 to 110 degrees when the one or more analytical regions are set at each of the forehead and the glabella, in eight directions in an angle ranges of 0 to 45 degrees and 115 to 165 degrees when the one or more analytical regions are set at the tail of the eye, and in six directions in an angle ranges of 45 to 60 degrees and 120 to 140 degrees when the one or more analytical regions are set at the corner of the mouth.

10. The wrinkle detection method according to claim 6, wherein the wrinkle direction edge filters are set in three directions in an angle range of 70 to 110 degrees when the one or more analytical regions are set at each of the forehead and the glabella, in eight directions in an angle ranges of 0 to 45 degrees and 115 to 165 degrees when the one or more analytical regions are set at the tail of the eye, and in six directions in an angle ranges of 45 to 60 degrees and 120 to 140 degrees when the one or more analytical regions are set at the corner of the mouth.

11. The wrinkle detection method according to claim 2, wherein after the wrinkle component emphasized images in which the wrinkle components are emphasized are produced, noise is eliminated from each of the wrinkle component emphasized images based on wrinkle shape information set in advance, and the wrinkle component emphasized images from which the noise has been eliminated are combined.

12. The wrinkle detection method according to claim 2, wherein after the wrinkle component emphasized images in which the wrinkle components are emphasized are produced, noise is eliminated from each of the wrinkle component emphasized images by multiresolution method, and the wrinkle component emphasized images from which the noise has been eliminated are combined.

13. The wrinkle detection method according to claim 2, wherein after the one or more analytical regions are set on the face, noise in the one or more analytical regions are eliminated by Gaussian filtering or by performing quadric surface approximation on background luminance distribution, and the wrinkle component extracted images are produced from the one or more analytical regions, from which the noise has been eliminated, by extracting the wrinkle components.

14. A wrinkle evaluation method, comprising the steps of:
calculating amounts of characteristics of wrinkles detected by the wrinkle detection method according to claim 1; and
evaluating degree of wrinkling by comparing the calculated amounts of characteristics with an average value of amounts of characteristics of wrinkles for a person at an age of the subject.

15. A wrinkle detection apparatus, comprising:
a luminance image conversion circuit adapted to convert an image acquired by imaging a face of a subject into a luminance image;
a face detection circuit adapted to detect the face from the luminance image;
an analytical region setting circuit adapted to set one or more analytical regions on the detected face;
a memory storing therein in advance angle ranges in which wrinkles tend to extend and which are set for respective portions of a face;
a wrinkle extraction circuit adapted to read out from the memory an angle ranges corresponding to each of the portions at which the one or more analytical regions have been set by the analytical region setting circuit and process each of the one or more analytical regions with a plurality of wrinkle direction edge filters of plural directions at different angles in the read out angle range to produce a plurality of wrinkle component extracted images by, from the set one or more analytical regions, extracting wrinkle components extending in one direction or in plural directions at different angles in the read out angle range;
a wrinkle emphasizing circuit adapted to produce a plurality of wrinkle component emphasized images corresponding to the wrinkle component extracted images, respectively, by emphasizing the wrinkle components and produce a composite image by combining the wrinkle component emphasized images; and
a wrinkle determination circuit adapted to detect a wrinkle component having an intensity equal to or greater than a predetermined threshold value from the composite image as a wrinkle of the subject.

16. A wrinkle evaluation apparatus, comprising:
the wrinkle detection apparatus according to claim 15; and
a wrinkle evaluation circuit adapted to evaluate degree of wrinkling by calculating amounts of characteristics of a wrinkle detected by the wrinkle detection apparatus and comparing the calculated amounts of characteristics with an average value of amounts of characteristics of wrinkles for a person at an age of the subject.

17. A non-transitory recording medium having stored therein a wrinkle detection program causing a computer to implement:
- a step of storing in a memory in advance angle ranges in which wrinkles tend to extend and which are set for respective portions of a face;
- a step of obtaining face data of a subject;
- a step of setting one or more analytical regions on the obtained face data;
- a step of reading out from the memory an angle ranges corresponding to each of the portions at which the one or more analytical regions have been set;
- a step of processing each of the one or more analytical regions with a plurality of wrinkle direction edge filters of plural directions at different angles in the read out angle range to produce plural pieces of wrinkle component extracted data by, from the set one or more analytical regions, extracting wrinkle components extending in one direction or in plural directions at different angles in the read out angle range;
- a step of producing plural pieces of wrinkle component emphasized data corresponding to the pieces of wrinkle component extracted data, respectively, by emphasizing the wrinkle components;
- a step of producing composite data by combining the pieces of wrinkle component emphasized data; and
- a step of detecting a wrinkle component having an intensity equal to or greater than a predetermined threshold value from the composite data as a wrinkle of the subject.

18. A non-transitory recording medium having stored therein a wrinkle evaluation program causing a computer to implement:
- a step of calculating amounts of characteristics of the wrinkle detected by the wrinkle detection program according to claim 17; and
- a step of evaluating degree of wrinkling by comparing the calculated amounts of characteristics with an average value of amounts of characteristics of wrinkles for a person at an age of the subject.

* * * * *